United States Patent
Argenta et al.

[11] Patent Number: 5,807,230
[45] Date of Patent: Sep. 15, 1998

[54] MULTI-PURPOSE WASTE DISPOSAL SYSTEM

[76] Inventors: Louis Argenta, 525 Knobview, Winston-Salem, N.C. 27103; Michael J. Morykwas, 6147 Spring Forest Dr., Pfafftown, N.C. 27040

[21] Appl. No.: 644,229

[22] Filed: May 10, 1996

[51] Int. Cl.[6] .................................. A62D 3/00; B09B 3/00
[52] U.S. Cl. .................... 588/258; 588/252; 588/259; 604/319; 604/320; 604/321
[58] Field of Search ................ 405/52, 128; 588/249, 588/252, 258, 259, 900; 604/317, 319, 320, 321

[56] References Cited

U.S. PATENT DOCUMENTS

| | | | |
|---|---|---|---|
| 4,525,100 | 6/1985 | Zawadzki, Jr. et al. | 588/249 |
| 4,795,448 | 1/1989 | Stacey et al. | 604/319 |
| 5,191,156 | 3/1993 | Jorgensen et al. | 588/249 |
| 5,245,117 | 9/1993 | Withers et al. | 588/249 |
| 5,262,578 | 11/1993 | Hall | 588/258 X |
| 5,434,339 | 7/1995 | La Motte et al. | 588/258 |
| 5,437,836 | 8/1995 | Yamada | 604/319 X |
| 5,573,349 | 11/1996 | Paoluccio | 588/249 X |

FOREIGN PATENT DOCUMENTS

455326  11/1991  European Pat. Off. ............... 588/258

*Primary Examiner*—George A. Suchfield
*Attorney, Agent, or Firm*—Charles W. Calkins; Kilpatrick Stockton LLP

[57] ABSTRACT

Disclosed are waste disposal devices for minimizing contamination of an operating room table with blood and body fluids during and after a surgery while substantially reducing the volume of medical waste and disposable materials generated by surgery. In one embodiment the device includes a bag constructed to fit an operating room table having u-shaped margins for collecting fluid runoff, a drainage tube with valve and a closure means for sealing the bag. Upon completion of the surgery, the bag is quickly and easily removed and completely sealed to enclose contaminated fluids and draperies generated by surgery. Prior to disposal, the contaminated fluids and trapped air are vacuumed from the sealed bag thereby substantially minimizing the volume of the disposable material.

15 Claims, 7 Drawing Sheets

MULTI-PURPOSE WASTE DISPOSAL SYSTEM

FIELD OF INVENTION

The subject invention is generally related to contamination and waste disposal devices and is more particularly directed to contamination and waste disposal devices for use in a medical setting such as an operating room.

BACKGROUND

There are thousands of medical operations performed daily in the United States. In each case, it is vital that all surfaces, particularly the operating room table, are clean and free from contamination. At the present time, either disposable drapes or cloth drapes are used in the operating room. Typically, bottom draperies are positioned beneath the patient and sterile top draperies are placed over the patient. While the draperies may absorb some of the fluid spillage common during the course of an operation, very frequently, blood and/or body fluids soak through or around the draperies so as to spill onto the operating room table or floor. Thus, after a major case, particularly when there is significant blood loss or irrigation fluids used, it is not unusual for the operating room table and floor to be contaminated with such fluids.

Typically, it takes a nurse approximately 15–30 minutes to wash and decontaminate the operating room table between cases. In addition, there is blood and other fluid spillage onto the floor both at the time of surgery and at the time the patient is moved and draperies are removed from the patient into appropriate waste containers. Nurses and operating room personnel must handle this contaminated material between the operating room table and into plastic bags into which they are placed for disposal. Once disposable drapes are placed into a plastic bag, the plastic bag is transferred to a heavy cardboard box for incineration or disposable. This results in disposable materials having considerable volume. Similarly, when cloth draperies are used, the blood soaked and wet cloth draperies are moved into plastic or cloth bags. Clearly, the manipulation of blood/body fluids and contaminated draperies into appropriate containers for disposal increases the risk of exposure and contamination of operating room personnel and the operating room.

Further, blood/body fluids, contaminated draperies and disposables must be isolated for incineration or disposal. The amount of blood on or in the disposables determine the costs for disposing of the materials. For example, greater than 20 cc of blood per unit may require special handling and result in considerable more expense for disposal. Thus, it is desirable to minimize the amount of blood component in disposables to reduce contamination and the cost of disposal.

Therefore, there is a need for a device which minimizes contamination of the operating room table and personnel while substantially reducing the volume of medical waste and disposable materials generated by surgery.

SUMMARY OF THE INVENTION

The aforementioned needs are met, and other advantages achieved by the present invention.

The subject invention is directed to a waste disposal device advantageous for use by operating room personnel for minimizing contamination of an operating room with blood and/or body fluids during surgery and substantially reducing the volume of disposable material generated by surgery.

One embodiment of the present invention comprises an operating room table cover for covering an operating room table during the course of an operation and providing a sealed container for disposal of waste materials upon completion of the surgery. Heretofore, it was necessary for nurses and other operating room personnel to handle blood/body fluids and contaminated draperies generated by surgery while spending valuable time washing and decontaminating the operating room table between cases. The present invention minimizes the amount of cleanup time required between cases and allows contaminated materials to be disposed of in a minimal volume with minimal risk to operating room personnel or contamination of any equipment or the operating room itself.

Another embodiment of the present invention comprises a disposable waste receptacle, advantageous for receiving medical waste and holding the medical waste for disposal.

An advantage of the waste disposal device of the present invention is that the waste disposal device prevents or minimizes contamination of operating room personnel and hardware, reduces the volume of disposable material to decrease the cost of disposal and minimizes the amount of blood and body fluids in the disposed material thus decreasing the cost and contamination risk of the disposed materials.

Another advantage of the waste disposal device of the present invention is that the waste disposal device may comprise a liquid impervious bag specifically designed to fit the size and conformation of an operating room table and includes a pocket for collecting fluid runoffs, a drainage tube for releasing fluids and a closure means for sealing the bag.

A further advantage of the waste disposal device of the present invention is that the waste disposal device may be easily removed and sealed to encapsulate contaminated fluids and draperies generated by surgery for disposal while minimizing risk of exposure and contamination to operating room personnel and the operating room.

A still further advantage of the waste disposal device of the present invention is that the waste disposal device may comprise a one-way valve for collecting fluids in the device, for example during surgery, and releasing fluids and trapped air from the bag after it has been sealed.

Still another advantage of the waste disposal device of the present invention is that the waste disposal device may comprise a unique bag which allows fluid and trapped air to be decompressed from the bag and results in a marked constriction and diminution in size of the bag to minimize the volume of disposable materials and decreases the cost of disposal.

Other advantages and features of the present invention features will be readily apparent from the accompanying drawings and description.

DETAILED DESCRIPTION OF THE INVENTION

The waste disposal device of the present invention is described in more detail below with reference to embodiments advantageous for use in a surgical operating room setting.

According to the present invention, a device for covering an operating room table during surgery and collecting waste materials generated by the surgery comprises:

a. a liquid impervious bag adapted to be placed over the operating room table, said bag having a top, a base and outer margins, said margins being capable of being folded or shaped to define a pocket for trapping and collecting fluid runoff during surgery;

b. a drainage tube extending outward from the bag, said drainage tube including a valve for releasing fluids from the bag; and c. a closure means for quickly and easily sealing the bag upon completion of the surgery and disposing of the waste materials generated by the surgery and contained therein.

A preferred embodiment of the operating room table cover comprises a plastic bag (enclosure) which may be sterile or unsterile and is constructed to fit the size and conformation of the operating room table. The dimensions of the bag are such that it extends beyond the edges of the table on all sides, falling vertically toward the floor, similar to a tablecloth. The bag includes u-shaped or upturned margins along its border, which form a pocket extending around the perimeter of the operating room table. The pocket is designed to trap and collect blood and other fluid runoff during surgery. Preferably the operating room table cover further comprises closure means for sealing the enclosure, such as, by way of example, a ZIPLOC™ type closure.

It is advantageous for the operating room table cover of the present invention to be constructed in a manner that permits the enclosure to be easily removed and completely sealed upon conclusion of the surgical procedure, with minimal effort, contact with or manipulation of blood/body fluids and contaminated draperies on the part of operating room personnel.

In a preferred embodiment, the operating room table cover includes a drainage tube, extending outward from the bag for carrying the collected fluids away from the bag. The drainage tube incorporates a one-way valve for releasing fluids from the bag. The valve is adapted to be connected to a vacuum device, such as a typical operating room suction, which can be used during the course of the operation, to remove runoff fluids collected in the pocket. After the bag is sealed, the contaminated fluids and trapped air are drawn from the bag through the valve. The one-way valve prevents air from re-entering the bag, thus decreasing the volume of the materials which must be discarded.

In use, the device of the present invention is quickly and easily placed over the operating room table prior to positioning the patient and draperies. The bag is positioned so that the u-shaped margins will trap and collect fluid runoff, thus minimizing blood/body fluid spillage onto the floor. During the course of an operation, fluid that has collected in the pocket is removed through the drainage tube and released through the one-way valve at the base of the plastic bag. In the preferred embodiment, the valve is connected to a routine operating room suction to draw the collected fluids from the pocket through the drainage tube.

Upon completion of the procedure, the bag is removed from the table and completely sealed while enclosing contaminated fluids, draperies and a significant amount of air and forming a large sealed bag. In the preferred embodiment, the valve of the large sealed bag is attached to a vacuum and the contaminated fluids and trapped air are drawn from the bag. It is an important feature of the subject invention that a substantial amount of the blood and body fluids are removed prior to disposing of the sealed bag so that the amount of contaminating fluid to be discarded is minimized. In addition, a gelling material, such as, by way of example ISOLIZER, may be placed into the bag before it is sealed so that a gel is formed of the remaining wet materials. Thus, the waste disposal device of the subject invention effectively minimizes contamination of an operating room table with blood and/or body fluids during surgery and substantially reduces the amount of contaminated fluids in and the volume of disposable material generated by surgery.

Figure 1:
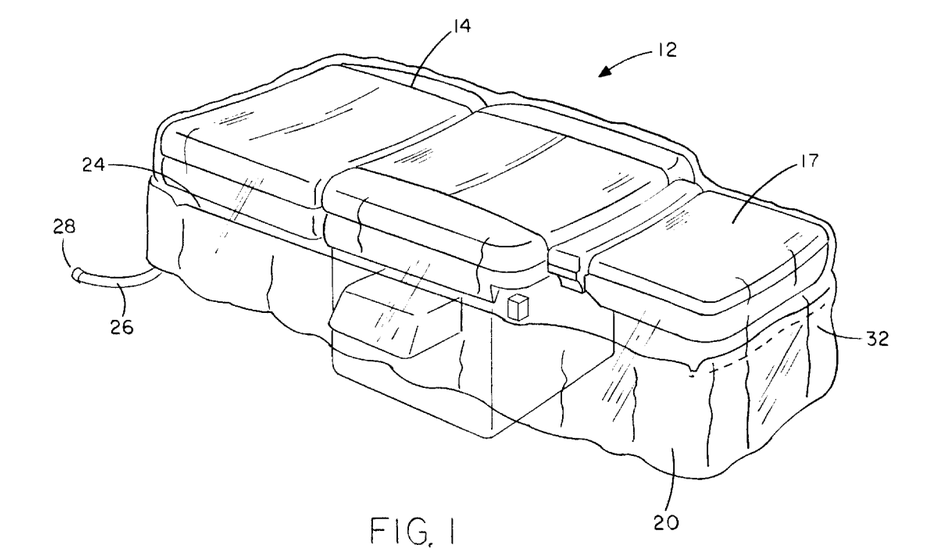
FIG. 1 is an illustration of an embodiment of the present invention for covering an operating room table in use as positioned on the table prior to surgery and placement of the draperies.
Figure 2:
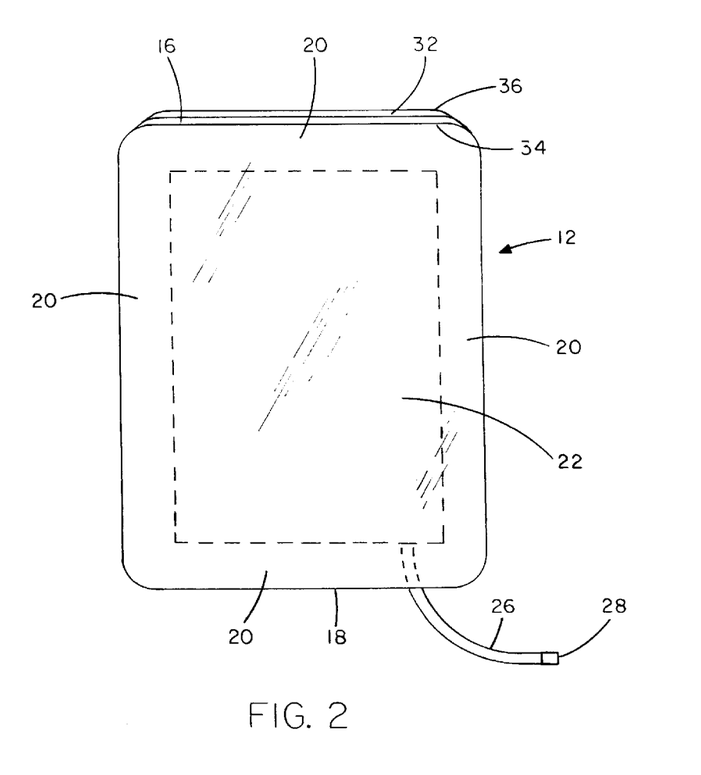
FIG. 2 is a perspective view of the embodiment depicted in FIG. 1 for covering an operating room table including a bag having a pocket along its margins, and a drainage tube at its base.
Figure 3:
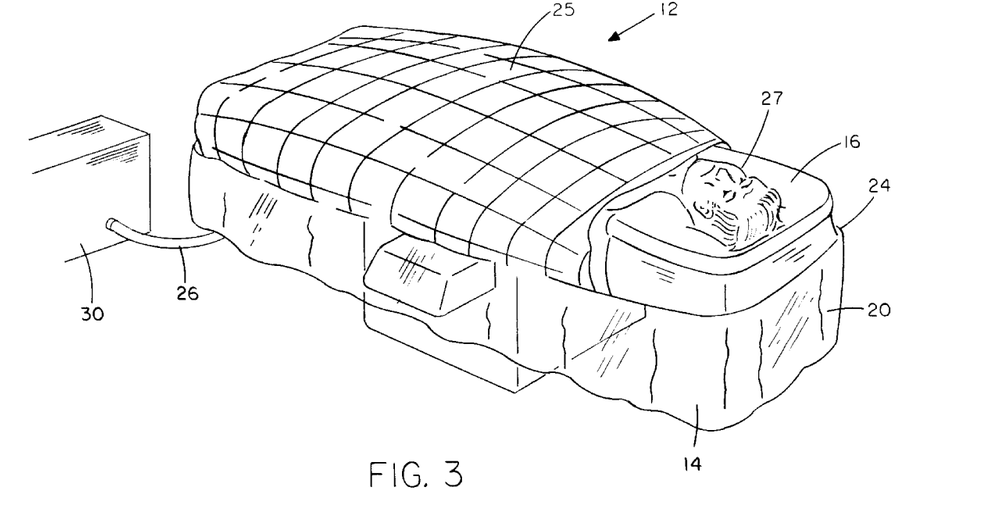
FIG. 3 is an illustration of the embodiment depicted in FIG. 1 for covering an operating room table with a patient and draperies positioned on the table, the ends of the draperies being placed in the pocket of the device and the valve connected to an operating room suction for removing fluids collected in the pocket during the operation.

Referring to FIGS. 1–3, the waste disposal device for covering an operating room table of the subject invention is designated generally by the reference numeral 12 and comprises and large, liquid impervious bag 14 which is specifically constructed to fit the size and conformation of an operating room table 17. The custom form bag 14 includes a top 16, a base 18, outer margins 20 and an interior portion 22. The outer margins 20 are upturned or u-shaped to form a pocket 24 which extends around the entire perimeter of the bag 14. As shown in FIGS. 1 and 3, the custom form bag 14 is sized so that the interior portion 22 covers the surface of the operating room table 17 while the outer margins 20 extend beyond the edges of the table 17 and fall vertically downward but do not reach the floor, similar to a tablecloth. As shown in FIG. 1 and FIG. 5A, closure means, 32 will be located underneath outer margins 20 while the bag is disposed over the table.

In a preferred embodiment, the bag 14 has a rectangular shape and dimensions of approximately 6 feet by 8 feet to enable the bag to fit on a conventional operating table. As will be realized from the description contained herein, the bag may be of other dimensions where desirable to fit other tables and/or apparatus. While the bag 14 is preferable made of a strong lightweight plastic material, such as polyethylene, or polymers comprising polyethylene, it will be understood that a variety of liquid impervious materials may be used.

In preparation for surgery, draperies 25 are typically positioned on the operating room table beneath a patient 27 and also over the patient. Once the bag 14 is properly positioned on the table 16 so that the pocket 24 traps and collects blood and other fluid runoff, the draperies 25 are placed over the bag 14. The patient 27 is then reclined on the draperies 25 and, after appropriate prepping, the patient is draped with sterile draperies 25. Rather than allowing the excess draperies 25 to extend onto the floor, the outer margins of the draperies 25 are placed into the pocket 24 of the plastic bag 14 (see FIG. 3). Thus, irrigation fluids that go on and under the draperies 25 are trapped and collected in the pocket 24 and not in the draperies 25.

Figure 4:
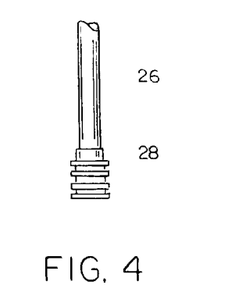
FIG. 4 is an enlarged, cross-sectional view of the drainage tube at the base of the embodiment of the present invention illustrated in FIG. 1 showing the one-way valve incorporated into the tube.

As shown in FIGS. 2 and 4, the device 12 of the subject invention includes a fluid transfer tube or drainage tube 26 extending outward from the bag 14. The drainage tube 26 is located at the base 18 of the bag 14 and preferably has an inner diameter of 0.1 to 1 inch, more preferably 0.25 to 0.5 inch. As best seen in FIG. 4, the drainage tube 26 includes a one-way valve 28 for releasing fluids from the bag 14 while preventing air from entering the bag through the drainage tube 26. The valve 28 is adapted to be connected to a vacuum device 30, such as a typical operating room suction. In the preferred embodiment, the valve 28 is connected to the operating room suction during surgery for drawing collected fluids from the pocket 24.

In addition, the device 12 of the subject invention includes a closure means 32 for quickly and easily sealing the bag 14 and disposing of the enclosed waste materials. In the preferred embodiment, the closure means 32 is located at the top 16 of the bag 14 when the edges of the bag are lifted and gathered for closing the bag, and includes a first closure element 34 and a second closure element 36 which is mateable with the first closure element 34, such as, by way of example a ZIPLOC™ closure device. ZIPLOC™ closures are a trademarked closure of Dow Chemical of Midland, Mich. While a ZIPLOC™ type closure is preferred, it will be understood that a variety of closure means can be used to seal the bag 14. The closure means, preferably a ZIPLOC™ type closure, are located a sufficient distance, generally 0.5 to 3 inches, preferably 1 inch, from the upper edges of the bag such that operating room personnel may lift the edges of the bag from the table and close the bag without coming into contact with any of the contents of the bag (See FIG 5A). For example, the closure means may be located approximately 1 inch from the upper edges of the bag and nurses can hold the outer inch, lift the edges of the bag straight up and close the bag without coming into contact with any of the contents fo the bag. Upon mating engagement of the first and second closure elements 34, 36, the contaminated materials are sealed within the bag 14. An advantage of the subject invention is that the bag 14 may be easily removed from the table 16 and completely sealed upon conclusion of the operation, with minimal effort or risk on the part of the operating room personnel.

Figure 5:
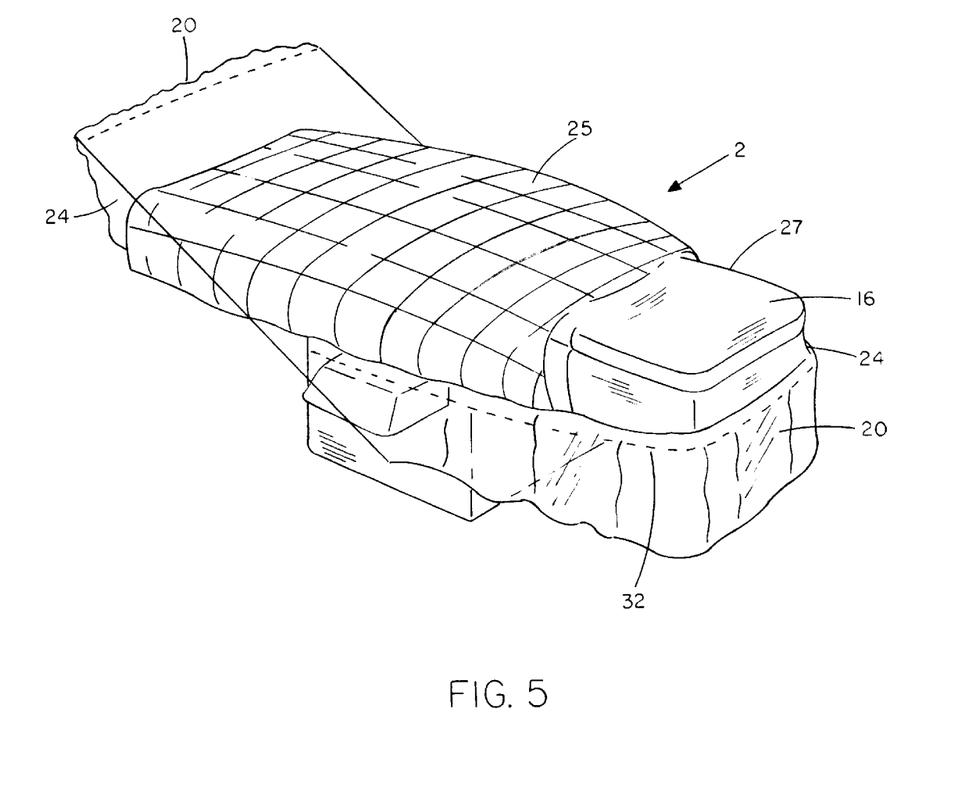
FIG. 5 is an illustration showing the margins of the embodiment of FIG. 1 being vertically lifted upon completion of the surgery so that fluids and the contaminated draperies are closed into the bag.
Figure 5A:
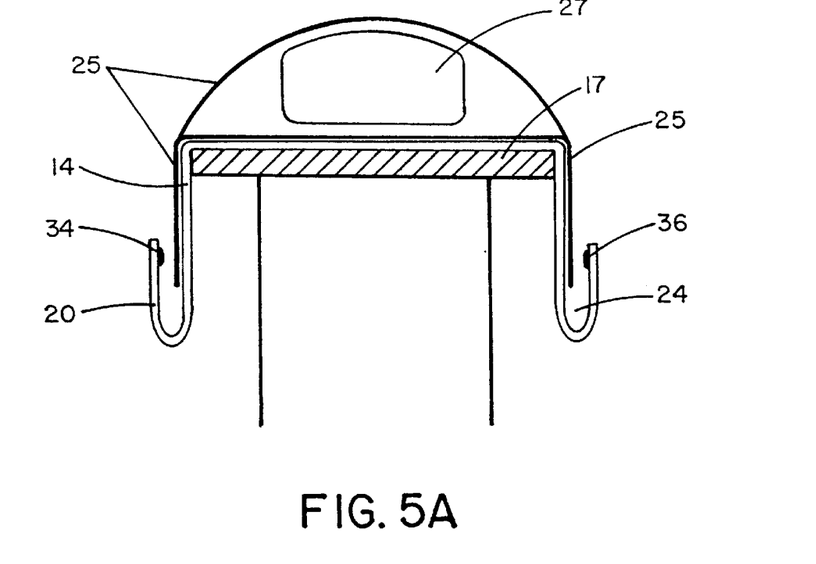
FIG. 5A is a cross-sectional view of the cover on the operating room table with the draperies positioned on the table and the ends of the draperies being placed into the pocket and showing the sealing means.
Figure 5B:
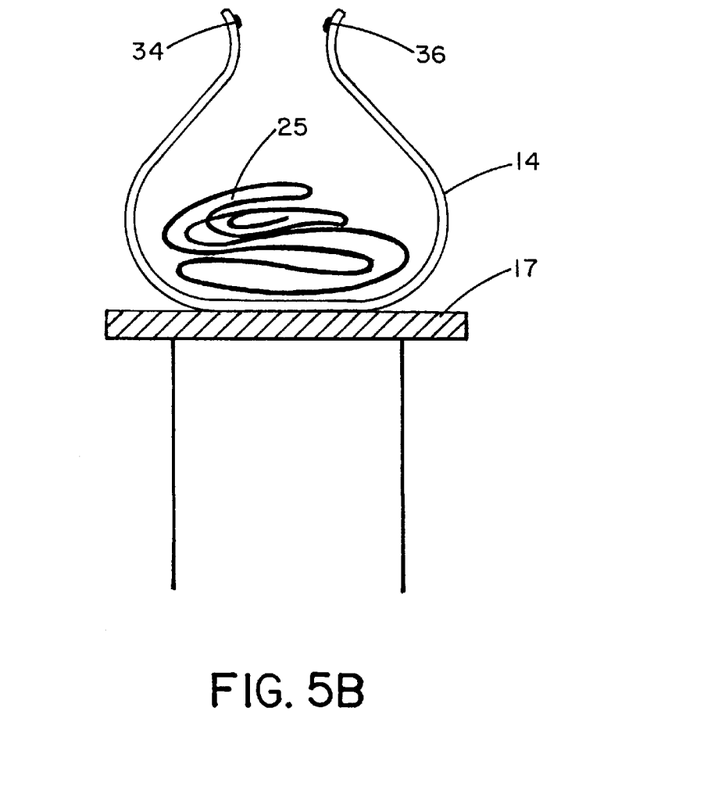
FIG. 5B is a perspective view of the cover depicted in FIG. 5A showing the contaminated draperies gathered within the cover and the sealing means at the top of the bag in position to be sealed.
Figure 6:
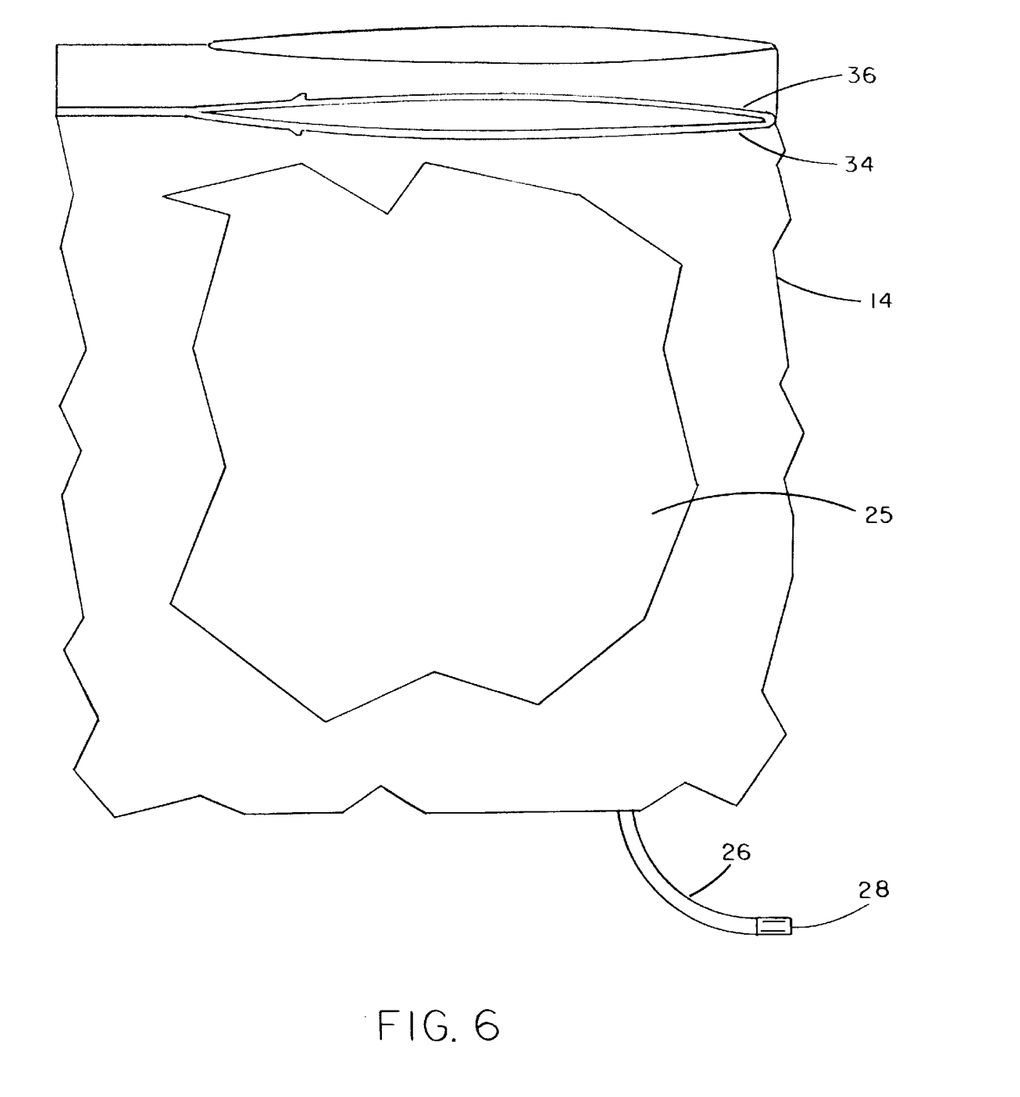
FIG. 6 is a perspective view of the embodiment depicted in FIG. 1 gathered to enclose fluids and the contaminated draperies and starting to be sealed by the partially mated closure means at the top of the bag to form a large sealed bag.
Figure 7:
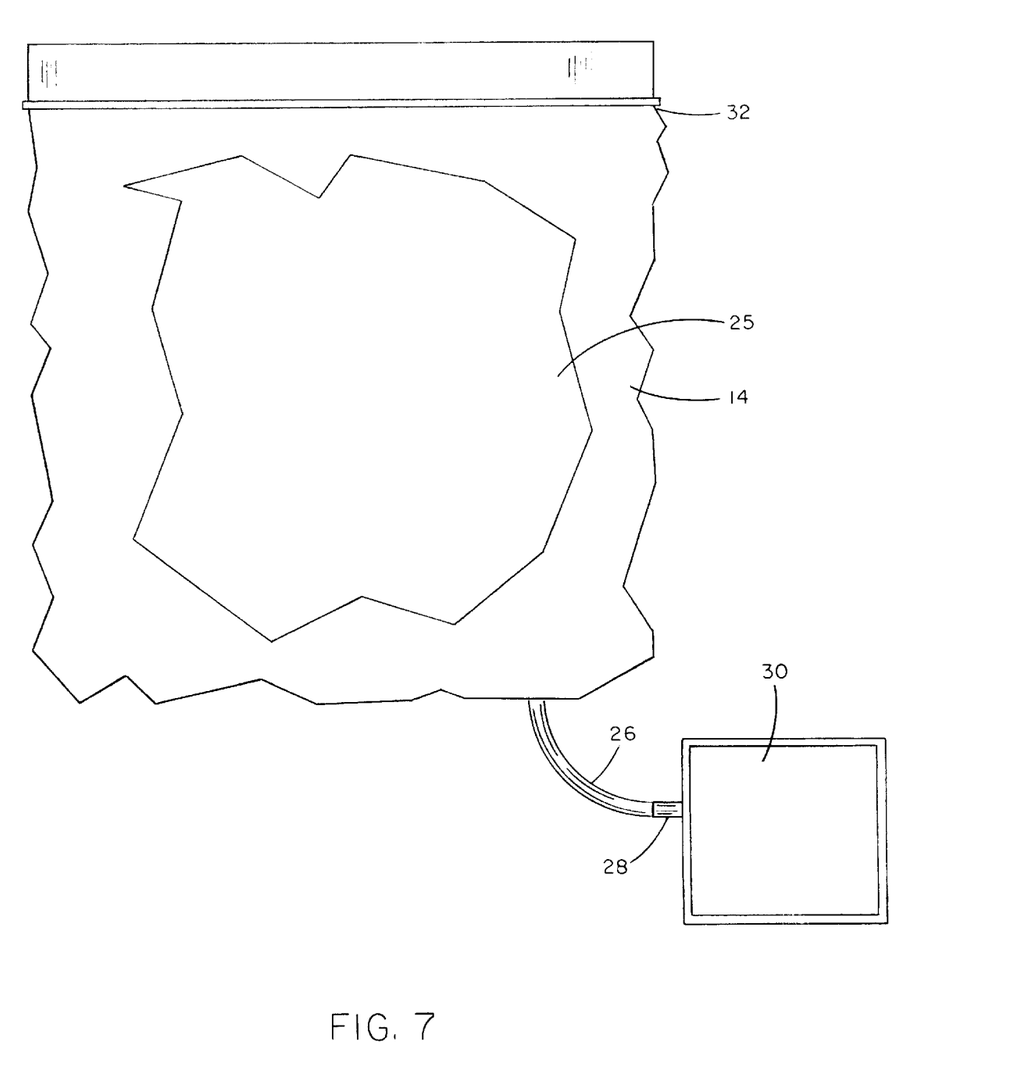
FIG. 7 is an illustration showing the valve of FIGS. 3 and 4 connected to a vacuum device for decompressing the fluids and trapped air from the bag after sealing.
Figure 8:
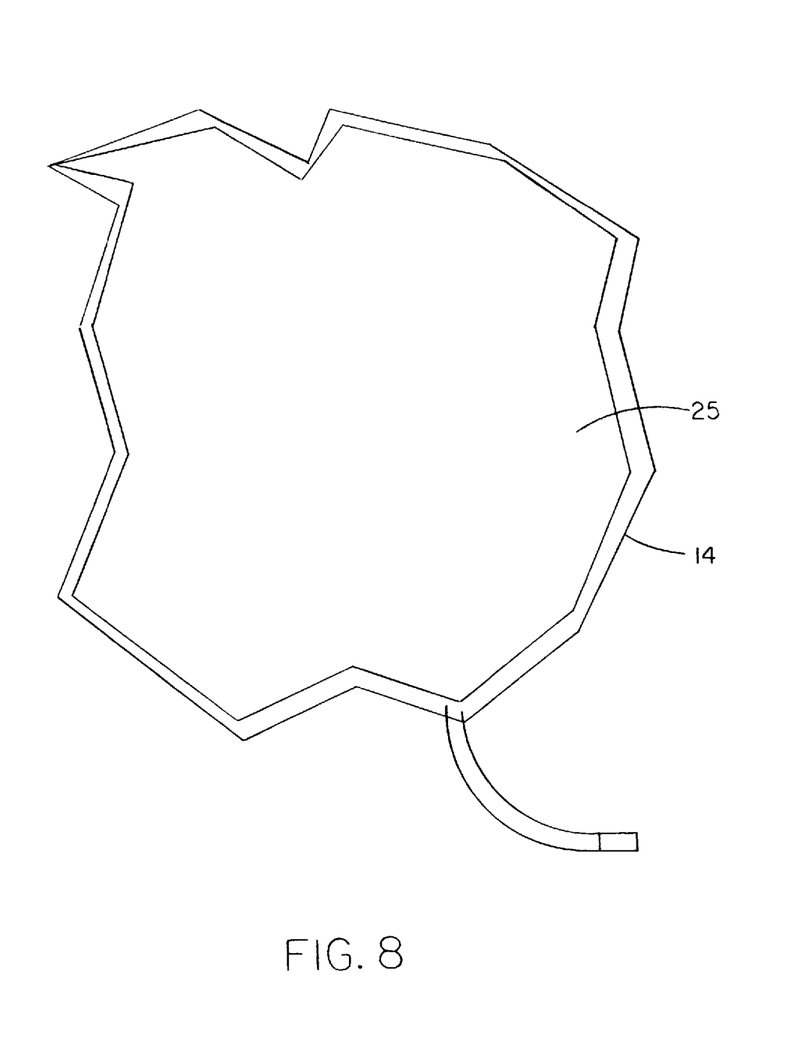
FIG. 8 is a perspective view of the embodiment of FIG. 1 reduced to a minimal volume after the fluids and trapped air have been removed.

Upon completion of the procedure and removal of the patient 27, the margins 20 of the plastic bag 14 are lifted vertically as illustrated in FIG. 5 and FIG. 5B, thus closing the contaminated draperies 25 and fluids into the plastic bag 14. As shown in FIG. 6, the bag 14 is gathered such that the first and second elements 34, 36 at the top of the bag are mated so that the bag 14 may be completely sealed and encapsulate the contaminated fluids, draperies 25 and a significant amount of air. Prior to sealing the bag 14, a gelling material (not shown) such as, by way of example ISOLIZER, may be placed into the bag 14 so that a gel is formed of the remaining wet materials, thus further reducing the amount of fluids to be disposed. Once the bag 14 is sealed, the valve 28 is connected to the vacuum device 30, as shown in FIG. 7, to create a seal and decompress both fluids and trapped air from the bag. As shown in FIG. 8, this results in a marked constriction and diminution in size of the bag 14, thus minimizing the volume of the disposable material and decreasing the disposal costs. Thus, the waste disposal device 12 of the subject invention effectively minimizes contamination of the operating room table 16 with blood and/or body fluids during the course of the operation and substantially reduces the amount of contaminated fluids in and the volume of disposable material generated by surgery.

According to the present invention, a disposable waste receptacle, advantageous for receiving medical waste and holding the medical waste for disposal comprises:

a liquid impervious receptacle;

means for sealing the receptacle;

a drainage tube extending outward from the receptacle, said drainage tube including a valve for releasing fluids from the bag.

The waste receptacle embodiment of the present invention may be produced from materials similar to those described above with reference to the operating room table cover embodiment of the present invention. The waste receptacle embodiment of the present invention may also be utilized in a similar fashion to the operating room table cover, in particular in the manner depicted in FIGS. 5, 6 and 7. Solid and liquid waste may be placed in the waste receptacle and then the waste receptacle sealed. After sealing, a vacuum apparatus may be attached to the drainage tube to withdraw fluids and air from the receptacle and thereby reduce the overall volume of the receptacle.

While specific embodiments and features of the invention have been disclosed herein, it will be readily understood that the invention encompasses all enhancements and modifications within the scope and spirit of the following claims.

What is claimed is:

1. A device for covering an operating room table during surgery and disposing of waste materials generated by surgery comprising:

a. a liquid impervious bag adapted to be placed over the operating room table, said bag having a top, a base and outer margins, said margins being shapeable to define a pocket for trapping and collecting fluid runoff during surgery;

b. a drainage tube extending outward from the bag, said drainage tube including a valve for releasing fluids from the bag; and c. a closure means for quickly and easily sealing the bag upon completion of the surgery and disposing of the waste materials generated by the surgery and contained therein.

2. The device of claim 1, wherein said valve is adapted for attachment with a vacuum device for drawing fluids from the bag during the surgery and after the bag is sealed.

3. The device of claim 2, wherein said valve comprises a one-way valve for allowing fluids to be released from the bag while preventing air from re-entering the bag after it is sealed.

4. The device of claim 2, wherein the drainage tube is positioned at the base of the bag.

5. The device of claim 2, wherein the closure means comprises a first closure element and a second closure element, said first and second closure elements being mateable whereby upon mating engagement of the elements, the bag is quickly and easily sealed.

6. The device of claim 5, wherein the closure means is positioned at the top of the bag.

7. The device of claim 2, wherein the bag is a plastic material.

8. The device of claim 5, wherein the bag is formed to the size and conformation of the operating room table.

9. The device of claim 8, wherein the bag has a rectangular shape with the dimensions being approximately 6 feet by 8 feet.

10. The device of claim 5, further comprising a gelling material positioned in the bag upon completion of the surgery.

11. The device of claim 2, wherein the vacuum device is an operating room suction apparatus.

12. A waste disposal device for minimizing contamination and reducing the volume of disposable materials comprising:
 a. a liquid impervious bag for containing solid and liquid waste materials;
 b. a drainage tube including a one-way valve for removing fluids from the bag; and
 c. a closure means for quickly and easily sealing the bag and disposing of the enclosed waste materials, said closure means including a first closure element and a second closure element, said first and second closure elements being mateable whereby upon mating engagement of the elements, the bag is quickly and easily sealed.

13. The device of claim 12, wherein the valve is adapted to be connected to a vacuum device for drawing fluids from the bag before and after the bag is sealed.

14. A method for use by operating room personnel for minimizing contamination of the operating room table and reducing the volume of waste material generated by surgery, the method comprising the steps of:
 a. utilizing a liquid impervious operating room table cover having outer u-shaped margins, a drainage tube with a valve and a closure means;
 b. placing the cover over the operating room table wherein the u-shaped margins are positioned to trap and collect fluid runoff;
 c. placing bottom covering drapes on the table cover, reclining a patient on the bottom drapes and placing top covering drapes over the patient;
 d. positioning the outer edges of the covering drapes in the u-shaped margins whereby the fluids are collected in the u-shaped margins;
 e. removing the patient upon completion of the surgery and leaving the contaminated covering drapes on the cover;
 f. lifting the margins of the cover vertically to enclose the contaminated covering drapes and fluids within the cover;
 g. sealing the closure means to form a large, sealed bag containing the contaminated materials and trapped air;
 h. attaching a vacuum to the valve and drawing the fluids from the sealed bag through the draining tube whereby the volume of material to be disposed is substantially decreased and forming a small, sealed bag; and
 i. disposing the small, sealed bag containing the contaminated material.

15. The method of claim 14, step (f) further comprising a step of adding a gelling material to gel the liquids contained in the bag.

* * * * *